(12) United States Patent
Cartier et al.

(10) Patent No.: US 6,881,577 B2
(45) Date of Patent: Apr. 19, 2005

(54) METHOD FOR IMPROVING TRANSFECTION EFFICIENCY

(75) Inventors: Regis Cartier, Berlin (DE); Michael Böttger, Berlin (DE); Annekathrin Haberland, Berlin (DE); Regins Reszka, Schwanebeck (DE)

(73) Assignee: Max-Delbrück-Centrum für Molekulare Medizin, Berlin (DE)

( * ) Notice: Subject to any disclaimer, the term of this patent is extended or adjusted under 35 U.S.C. 154(b) by 0 days.

(21) Appl. No.: 10/312,691

(22) PCT Filed: Jun. 28, 2001

(86) PCT No.: PCT/DE01/02336

§ 371 (c)(1),
(2), (4) Date: Mar. 10, 2003

(87) PCT Pub. No.: WO02/00991

PCT Pub. Date: Jan. 3, 2002

(65) Prior Publication Data

US 2003/0175975 A1 Sep. 18, 2003

(30) Foreign Application Priority Data

Jun. 28, 2000 (DE) .......................................... 100 31 900
Aug. 18, 2000 (DE) .......................................... 100 40 895

(51) Int. Cl.$^7$ .............................................. C12N 15/64
(52) U.S. Cl. .......................... 435/458; 514/44; 530/317

(58) Field of Search .......................... 435/458; 514/44; 530/317

(56) References Cited

U.S. PATENT DOCUMENTS

| 5,228,211 A | 7/1993 | Stubbing |
| 5,736,392 A | 4/1998 | Hawley-Nelson et al. |
| 6,022,735 A | 2/2000 | Curiel et al. |

FOREIGN PATENT DOCUMENTS

| DE | 36 32 820 A | 4/1988 |
| DE | 42 35 560 A | 4/1994 |
| EP | 0 094 356 A | 11/1983 |
| EP | 0 545 016 A1 | 6/1993 |
| WO | WO 94/23751 A1 | 10/1994 |
| WO | WO 98/35984 A2 | 8/1998 |
| WO | WO 99/53961 A1 | 10/1999 |

OTHER PUBLICATIONS

Chan et al., Human Gene Therapy, vol. 10, Jul. 1, 1999, pp. 1695–1702.*

* cited by examiner

*Primary Examiner*—James Ketter
(74) *Attorney, Agent, or Firm*—Birch, Stewart, Kolasch & Birch, LLP

(57) ABSTRACT

The invention relates to a method for improving transfection efficiency through the use of K16-peptides. In addition, the invention further relates to novel K16-peptides, including a K16-CYC peptide.

6 Claims, 16 Drawing Sheets

METHOD FOR IMPROVING TRANSFECTION EFFICIENCY

This application is the national phase under 35 U.S.C. § 371 of PCT International Application No. PCT/DE01/02336 which has an International filing date of Jun. 28, 2001, which designated the United States of America.

BACKGROUND OF THE INVENTION

The invention relates to a procedure for the improvement of the transfection efficiency through the use of K16-peptides. In addition, the invention includes novel K16-peptides. The fields of application are molecular biology and medicine.

The transfection mechanism of nonviral gene delivery systems is a complex process involving the passage through various biological barriers. One major factor limiting the efficiency of nonviral vectors is the nuclear envelope. The transfer of the vector into the nucleus finally permits the efficient expression of the transgene. One approach for plasmid DNA to overcome the nuclear envelope is to take advantage of nucleocytoplasmic transport mechanisms of the cell. One strategy is the non covalent attachment to the DNA of peptides carrying a NLS-sequence and containing an additional cationic DNA-binding domain. Subsequently, the bound NLS-sequence is believed to be recognized by the nuclear transport machinery which facilitates the nuclear transport of the DNA into the nucleus.

In nonviral gene delivery systems, one of the most utilized NLS-sequences is the amino acid sequence 126 to 132 of the Simian Virus 40 (SV 40) large T-antigen (SV 40-NLS). However, a NLS-sequence specific enhancement of the transfection efficiency based on this strategy was not conclusively demonstrated.

BRIEF SUMMARY OF THE INVENTION

The aim of the present invention was to improve the nuclear uptake of plasmid DNA. According to the invention a synthetic peptide was constructed consisting in an oligo-lysine DNA-binding domain and a SV 40-NLS. In addition, the construction and optimization of a complex was realized consisting in plasmid DNA, a synthetic peptide and lipid.

The synthetic peptides with the following amino acid sequences were used:

```
K16-NLS:
CKKKKKKKKKKKKKKKKGGGPKKKRKVG
(SEQ ID NO:1)

K16-SLN:
CKKKKKKKKKKKKKKKKGGGGVKRKKKP
(SEQ ID NO:2)

K16-Vpr:
KKKKKKKKKKKKKKKKCGGGIGCRHSRIGVTRQRRARNGASRS
(SEQ ID NO:3)

K16-VprN
KKKKKKKKKKKKKKKKGGGCNEWTLELLEELKNEAVRHF
(SEQ ID NO:4)

K16-mVprN
KKKKKKKKKKKKKKKKGGGNEATLELLPELKNPAVRHF
(SEQ ID NO:5)
```

All the mentioned peptides carry 16 lysine residues for the binding of the peptide to the plasmid DNA.

The K16-NLS peptide contains also the SV 40-NLS sequence (PKKKRKV—SEQ ID NO:8). The K16-SLN peptide is a control peptide which has an identical amino acid composition as K16-NLS. It carries the same DNA binding domain but contains an inversed SV 40-NLS sequence. The K16-Vpr peptide carries the mentioned oligo-lysine DNA binding domain and also a NLS sequence which was derived from the C-terminal domain of the HIV I-Vpr protein. The K16-VprN peptide carries in analogy to K16-Vpr a NLS sequence which was derived from the N-terminal domain of HIV I-Vpr. The K16-mVprN is a control peptide carrying the mentioned DNA-binding domain and a VprN-NLS- control sequence which was constructed after the replacement of three critical amino acid residues. As described previously this modification results in a peptide which is deficient in its ability to facilitate the nuclear import of a cargo.

Furthermore, a synthetic peptide constisting of 16 lysine residues (K16) was also used as an additional control peptide.

The lipid mixture cationic liposome (LIPOFECTIN®) was preferentially used as the lipid.

Complexes consisting in plasmid DNA, peptide and lipid were formed and used in transfection experiments of human colon carcinoma cells (HCT 116) in vitro. The luciferase reporter gene was used in order to measure the transfection efficiency.

In addition to the construction of the mentioned K16 peptides the invention consists in the construction of DNA-peptide-lipid-complexes. A critical issue is thereby the composition of the complexes through the selection of an appropriate peptide to DNA charge ratio as well as an appropriate amount of the lipid. The procedure of complex formation (involving concentrations, volume, buffer type, incubation time and the order by which the elements are sequentially added to the mixture, see FIGS. 1–3 and 4–6) is also a critical factor determining the transfection efficiency of the system.

After optimization of each factor an appropriate complex composition as well as an appropriate complex formation procedure was obtained leading to a NLS-sequence specific increase of the reporter gene expression following transfection of HCT 116 cells.

The invention consists in the selection of a peptide to DNA charge ratio resulting in relative unstable peptide/DNA-complexes to which a relatively small amount of lipid is subsequently added.

The resulting sequence specific enhancement of gene expression correlates with an increased nuclear transport of the DNA.

A further part of the present invention consists in the construction of a cyclic peptide for the stabilization of the NLS-sequence and its use for the optimization of a nonviral gene delivery system.

The SV 40-NLS sequence contains a relative high amount of basic residues and therefore, has a relatively strong positive charge under physiological conditions. As it was shown in transfection experiments as well as through biochemical studies the SV 40-NLS is likely to interact strongly with the plasmid DNA used in nonviral gene delivery systems. The binding of the SV 40-NLS to the DNA may sterically hinder the NLS in its interaction with the nuclear import machinery. In addition, the secondary structure of the NLS may also be altered so that it may not be recognized as a nuclear import substrate by the corresponding factors.

The invention consists in the stabilization of the secondary structure of the SV 40-NLS through the cyclization of the peptide. It is a known fact that the SV 40-NLS adapt to a β-sheet conformation upon interaction to its receptor importin α. The basis of the NLS-cyclization was the utilization of a cyclic peptide containing two antiparallel β-sheet sequences.

The invention consists in the reconstitution of the SV 40-NLS within the mentioned cyclic peptide. As a result, a cyclic peptide was created containing two antiparallel β-sheets sequences from which one side includes the SV 40-NLS. For binding of the peptide to the DNA 16 lysine residues were covalently attached to the β-sheet located to the opposite of the SV 40-NLS. Consequently, the resulting construct (K16-CYC) is a synthetic peptide consisting in a cyclic NLS-sequence and an oligo-lysine DNA-binding domain.

K16-CYC has the following sequence:

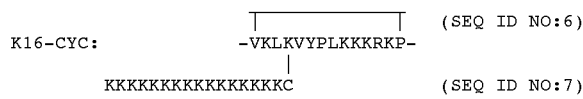

K16-CYC:         -VKLKVYPLKKKRKP-          (SEQ ID NO:6)
                 |
                 KKKKKKKKKKKKKKKKC          (SEQ ID NO:7)

Furthermore, the invention consists in the two following K16-peptides, the peptide containing 39 amino acids with the following sequence: K16-VprN: KKKKKKKKKKKKKKKKGGGCNEWTLEL-LEELKNEAVRHF (SEQ ID NO:4) and the peptide containing 38 amino acids with the following sequence: K16-mVprN: KKKKKKKKKKKKKKKKGGGNEATLELL-PELKNPAVRHF (SEQ ID NO:5).

These peptides are suitable for transfection experiments in combination with plasmid DNA as well as with plasmid DNA plus a lipid.

DETAILED DESCRIPTION OF THE INVENTION

In the following the invention is illustrated by different examples.

Utilization of the K16-CYC-Peptide in a Nonviral Gene Delivery System

Based on the above described procedure for the optimization of DNA-peptide-lipid-complexes different complexes containing plasmid DNA, the K16-CYC peptide and cationic liposome (LIPOFECTIN®) were formed and subsequently used in transfection experiments of HCT 116 cells.

Figure 1:
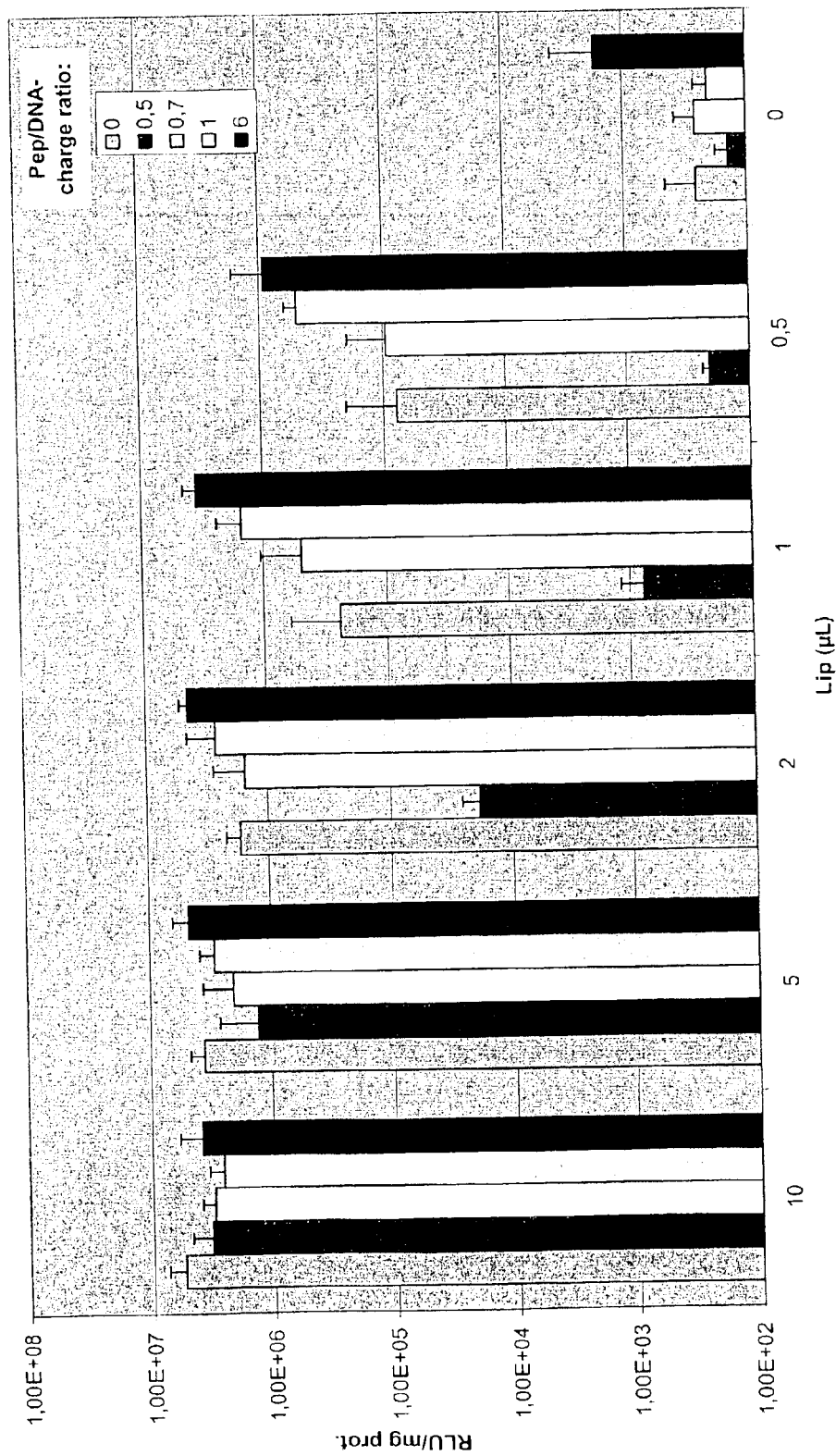
FIG. 1 shows transfection using K16-SNL/DNA/LIPOFECTIN-complexes for 15 min. of incubation.
Figure 2:
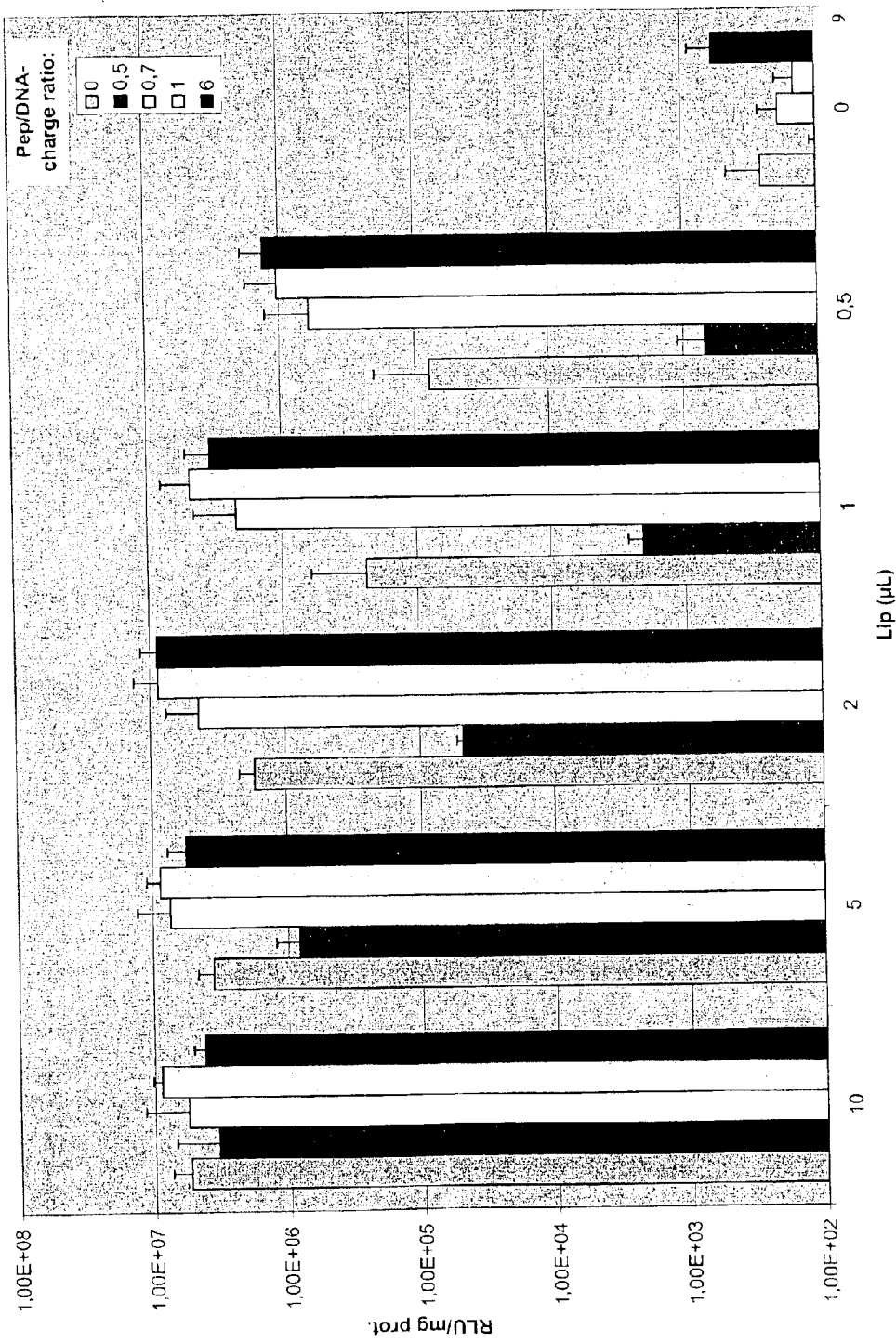
FIG. 2 shows transfection using K16-NLS/DNA/LIPOFECTIN-complexes for 15 min of incubation.
Figure 3A:
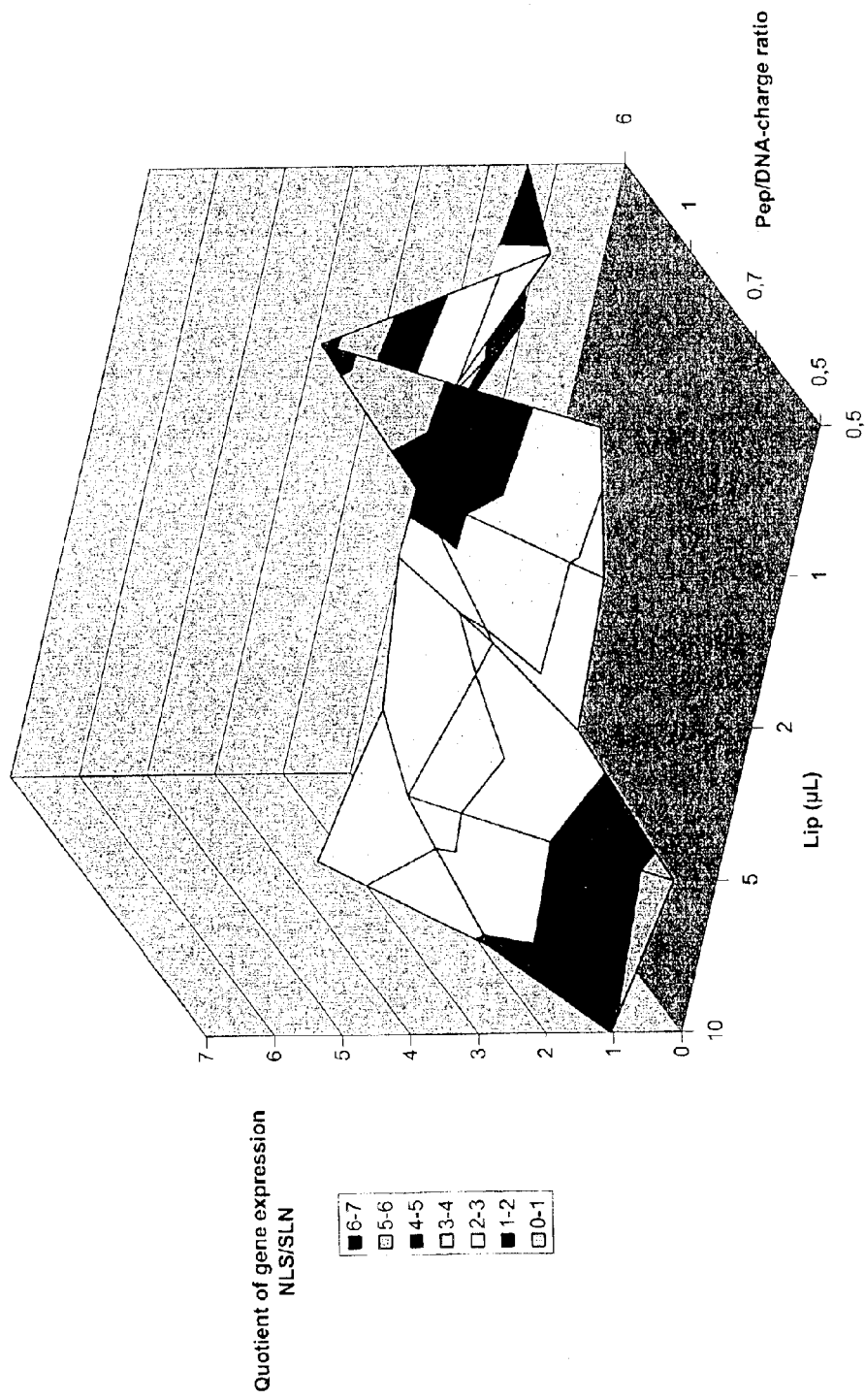
FIG. 3a shows sequence specific gene expression NLS/SLN, for 15 min. of incubation.
Figure 3B:
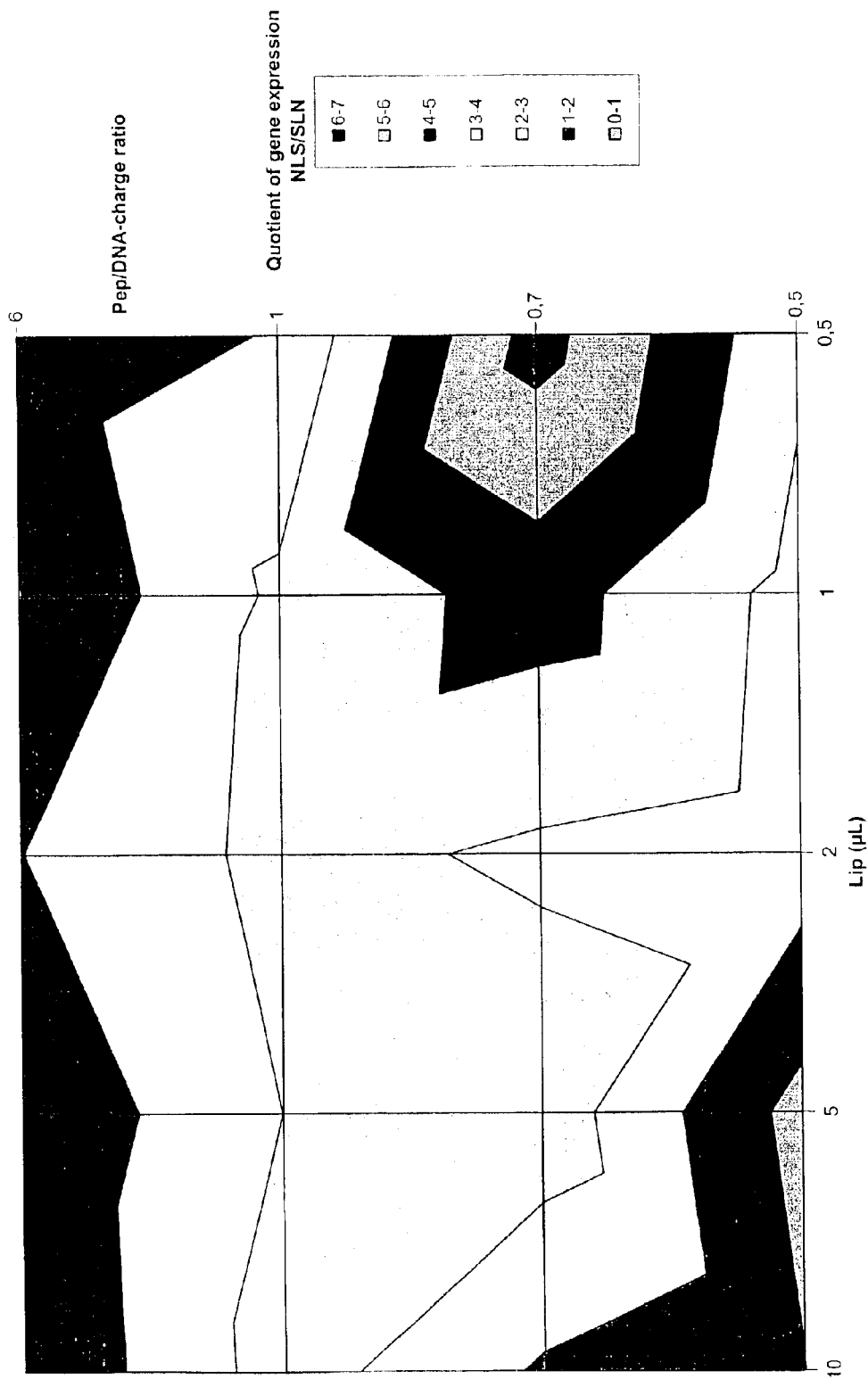
FIG. 3b shows sequence specific gene expression NLS/SLN, for 15 min. of incubation.
Figure 4:
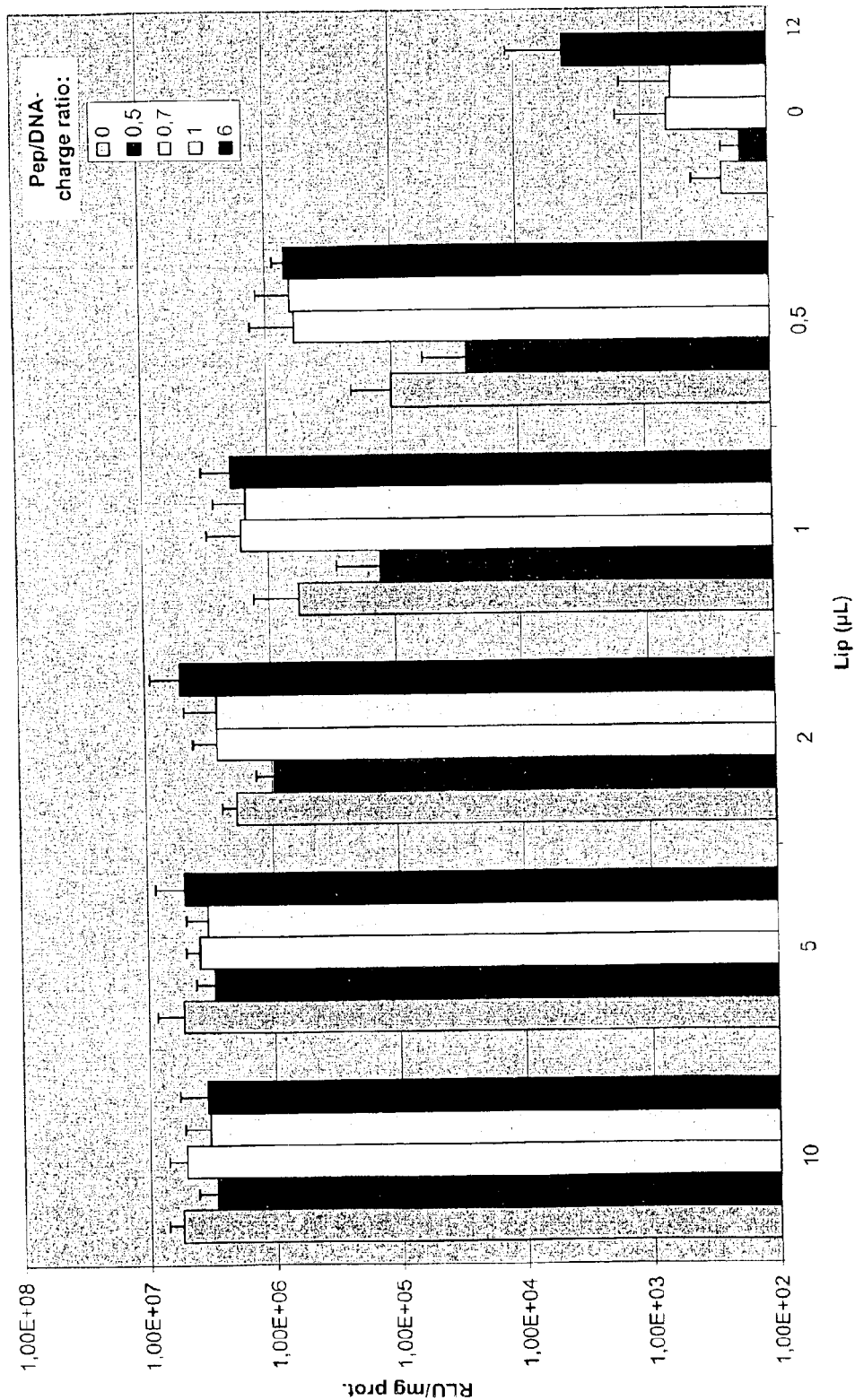
FIG. 4 shows transfection using K16-SNL/DNA/LIPOFECTIN-complexes.
Figure 5:
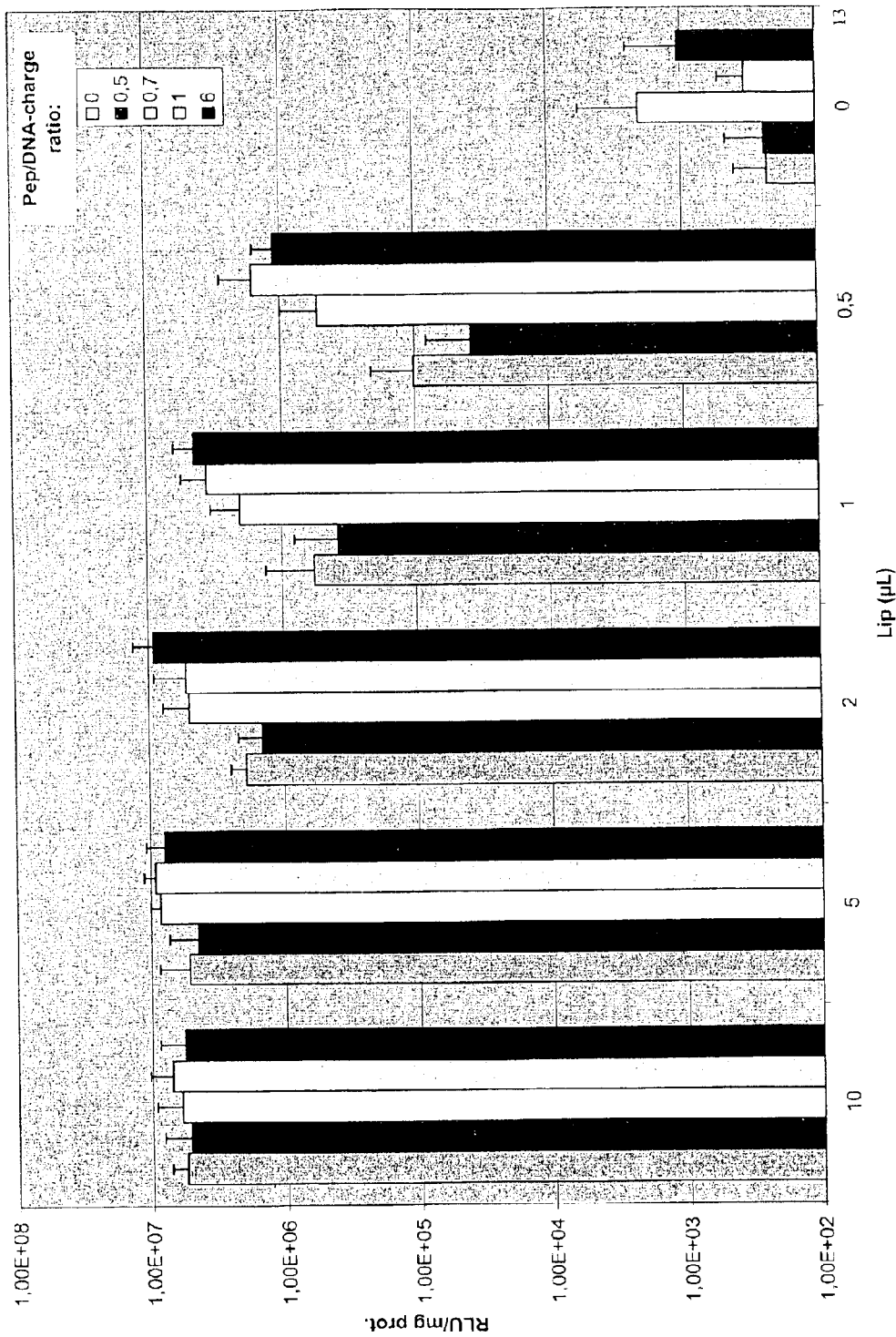
FIG. 5 shows transfection using K16-NLS/DNA/LIPOFECTIN-complexes
Figure 6A:
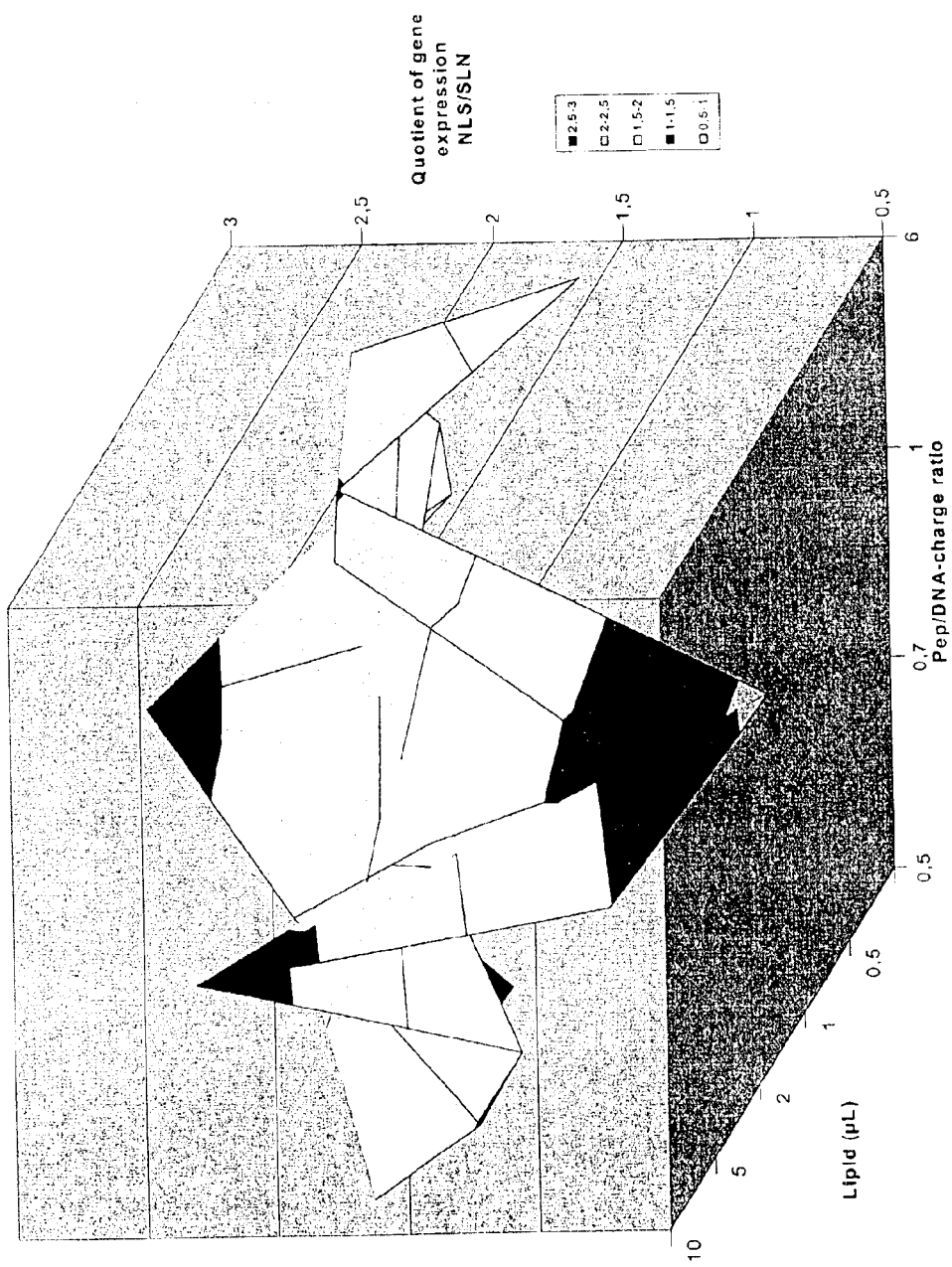
FIG. 6a shows sequence specificity of gene expression NLS/SLN.
Figure 6B:
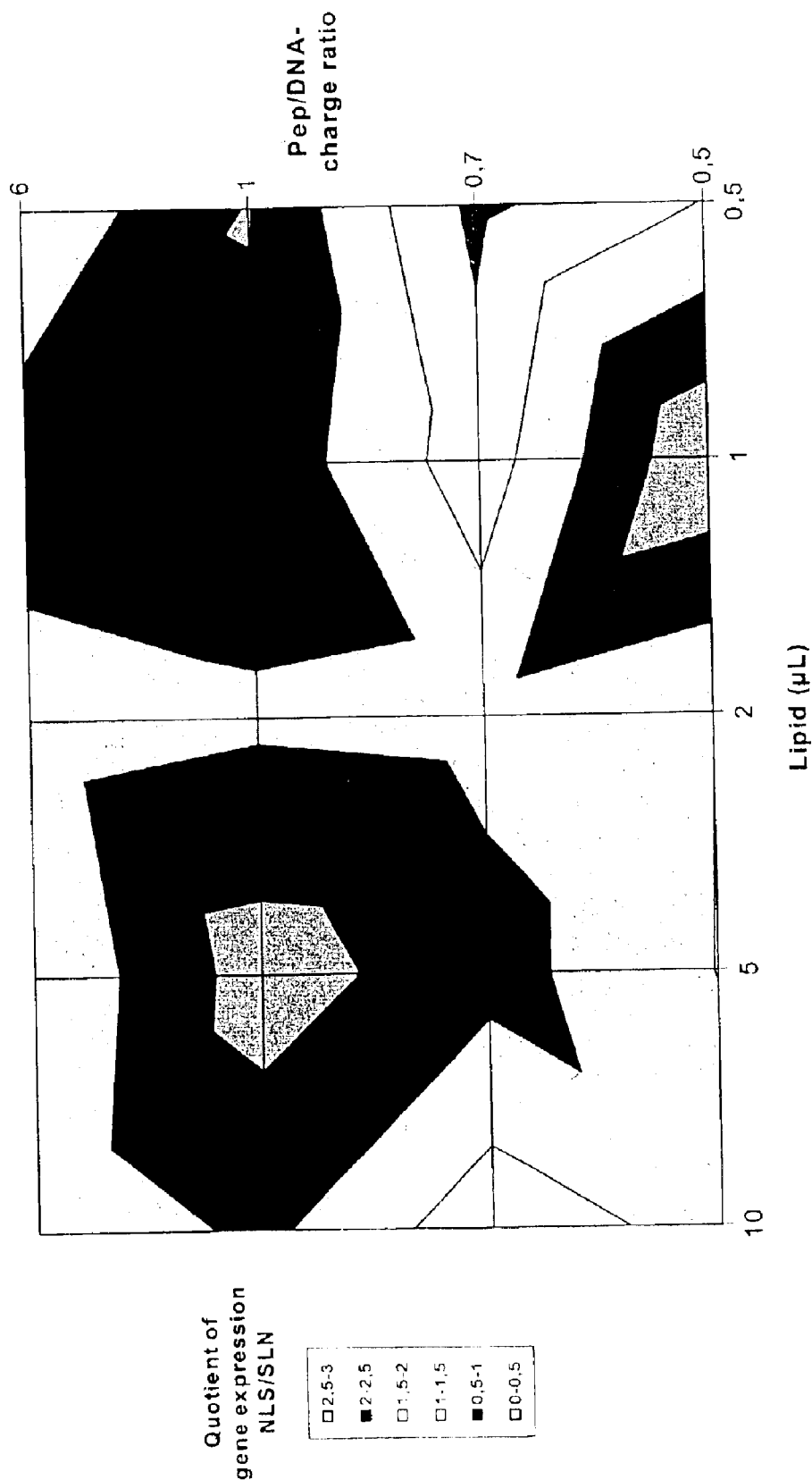
FIG. 6b shows sequence specificity of gene expression NLS/SLN.
Figure 7:
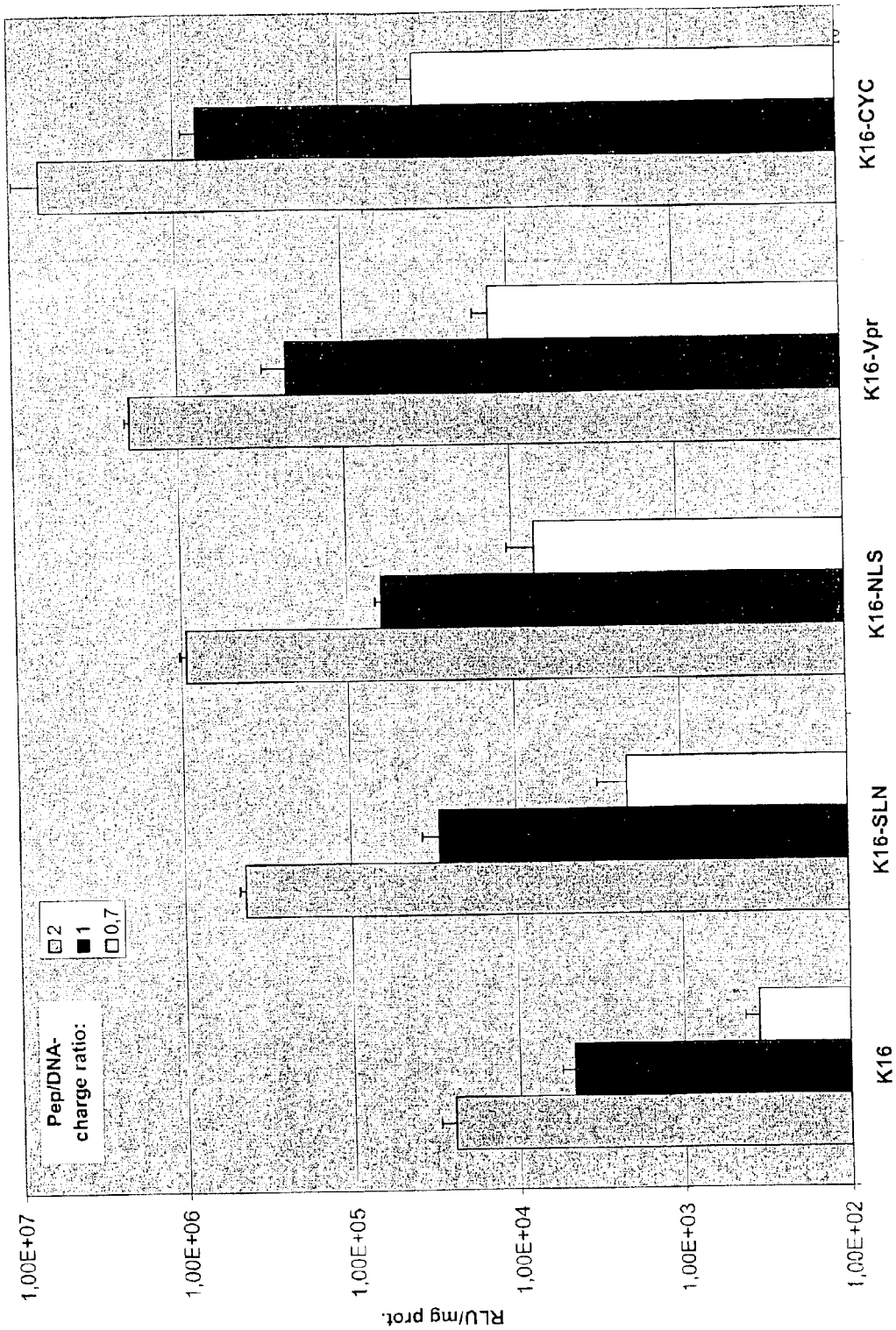
FIG. 7 shows polyplexes containing 0.5 μl LIPOFECTIN.
Figure 8:
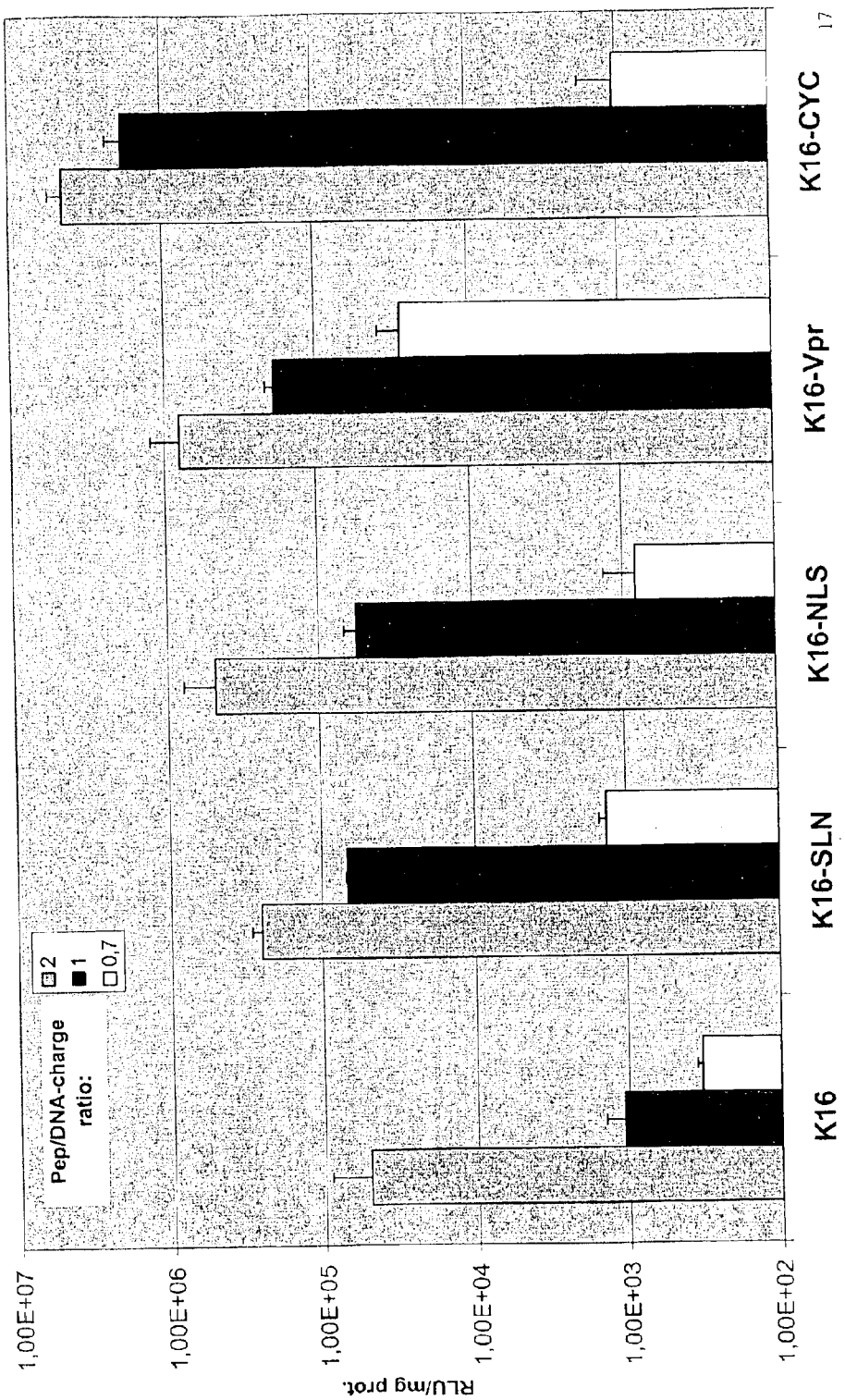
FIG. 8 shows polyplexes containing 1 μl LIPOFECTIN.

The results show a dramatic increase of the reporter gene expression following transfection using the K16-CYC peptide as compared to the K16-NLS peptide, the latter contains a linear form of the SV 40-NLS sequence (see FIGS. 7 and 8).

Utilization of the K16-VprN-Peptide in a Nonviral Gene Delivery System

Complexes were formed containing plasmid DNA, the K16-VprN peptide and cationic liposome (LIPOFECTIN®) and subsequently used in transfection experiments of HCT 116 cells.

Figure 9:
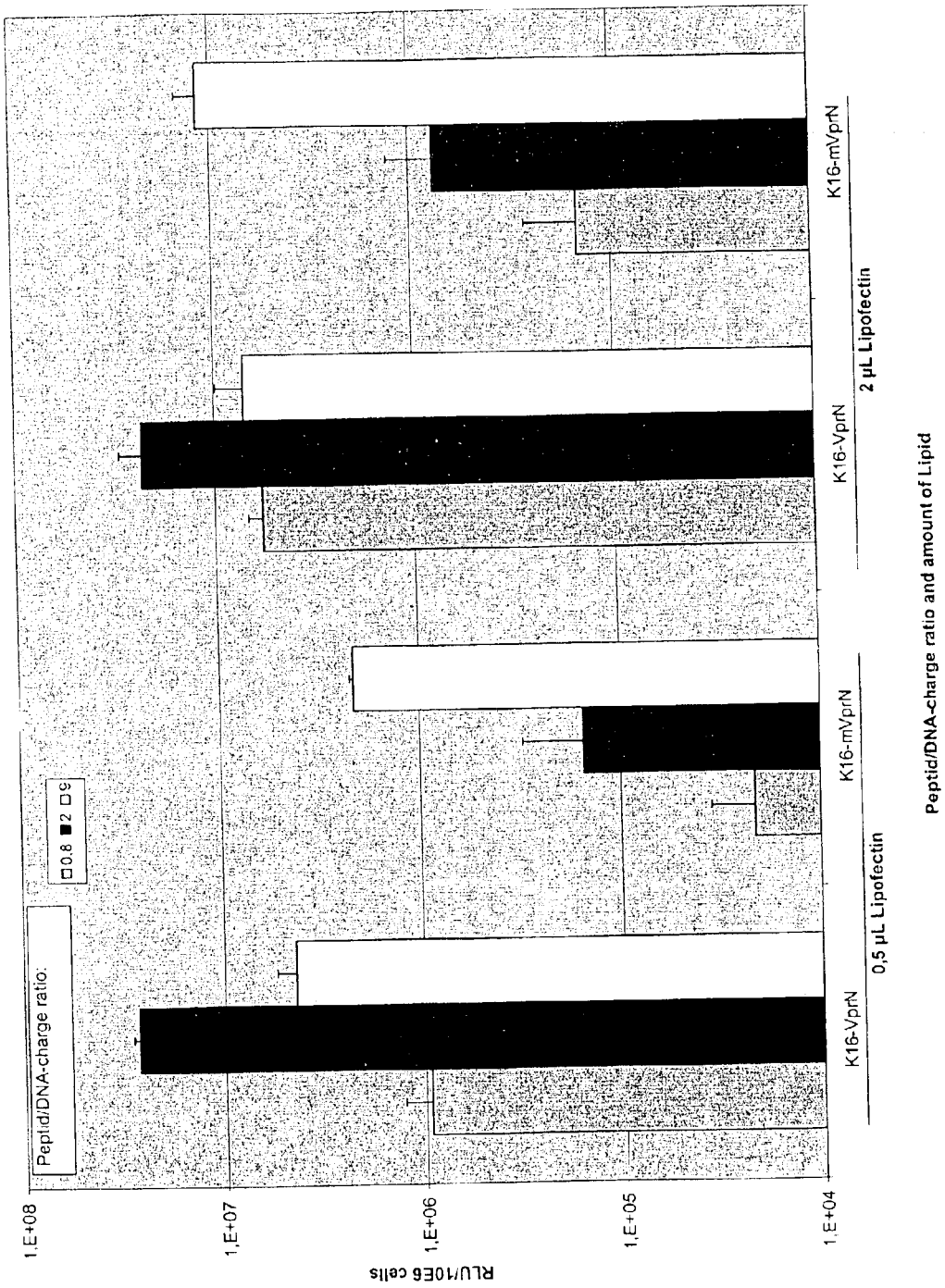
FIG. 9 shows luciferase-expression.

In both applications, the K16-mVprN peptide was used as a control peptide instead of the K16-VprN peptide. The results show a significant increase of the reporter gene expression as compared to the experiments were the control peptide was used (FIGS. 9 and 10).

Figure 10:
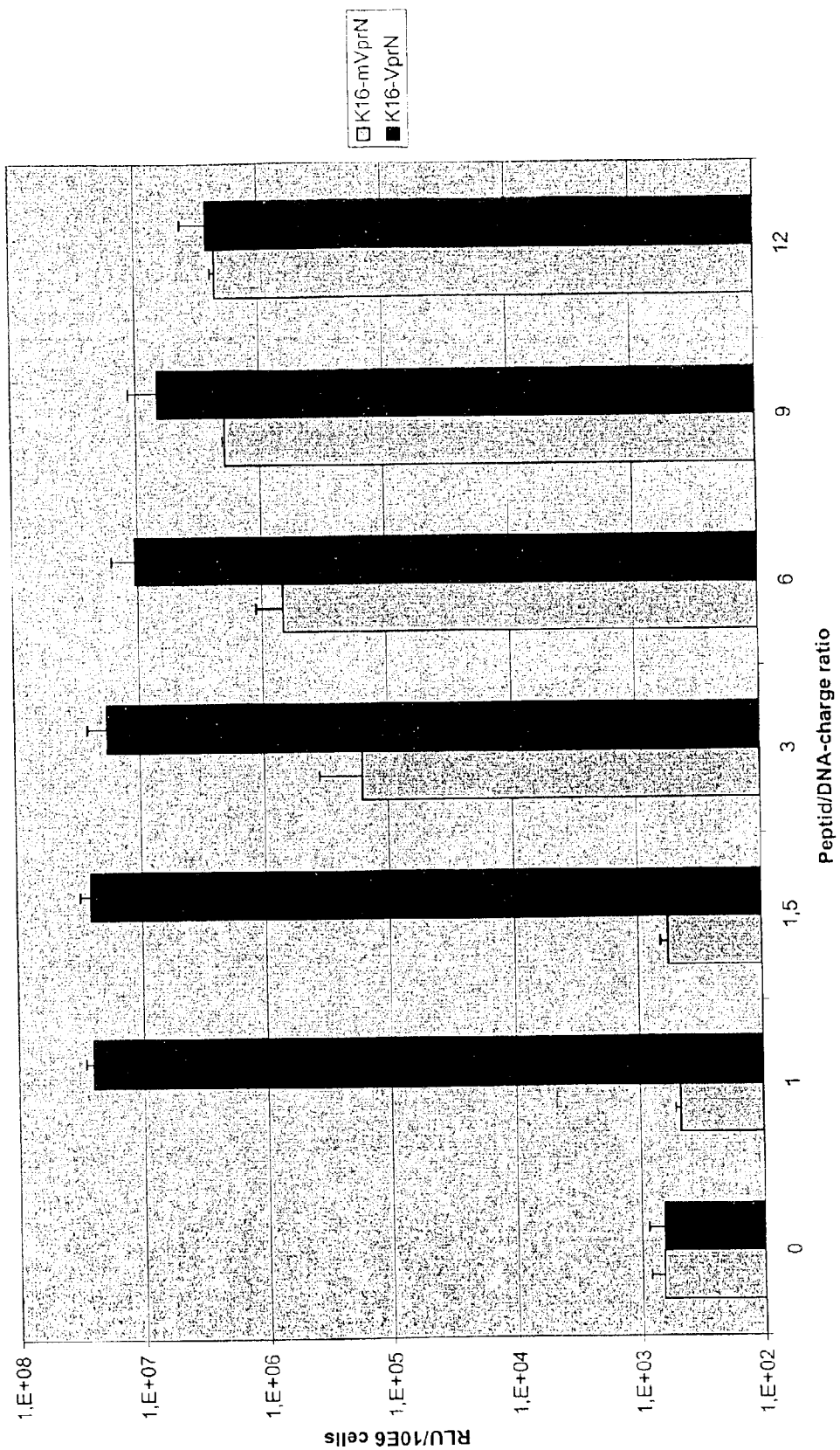
FIG. 10 shows luciferase-expression.

The NLS-sequence-specific enhancement of the transfection efficiency was observed in a greater extend in the case when the lipid was not added to the peptide/DNA-complex (FIG. 10). The K16-VprN peptide lead to a 10-fold increase of the maximum reporter gene expression level as compared to the K16-mVprN peptide. Moreover, in the case of K16-VprN the highest gene expression was obtained using a 12 times less amount of peptide as compared to K16-mVprN.

Figure 11:
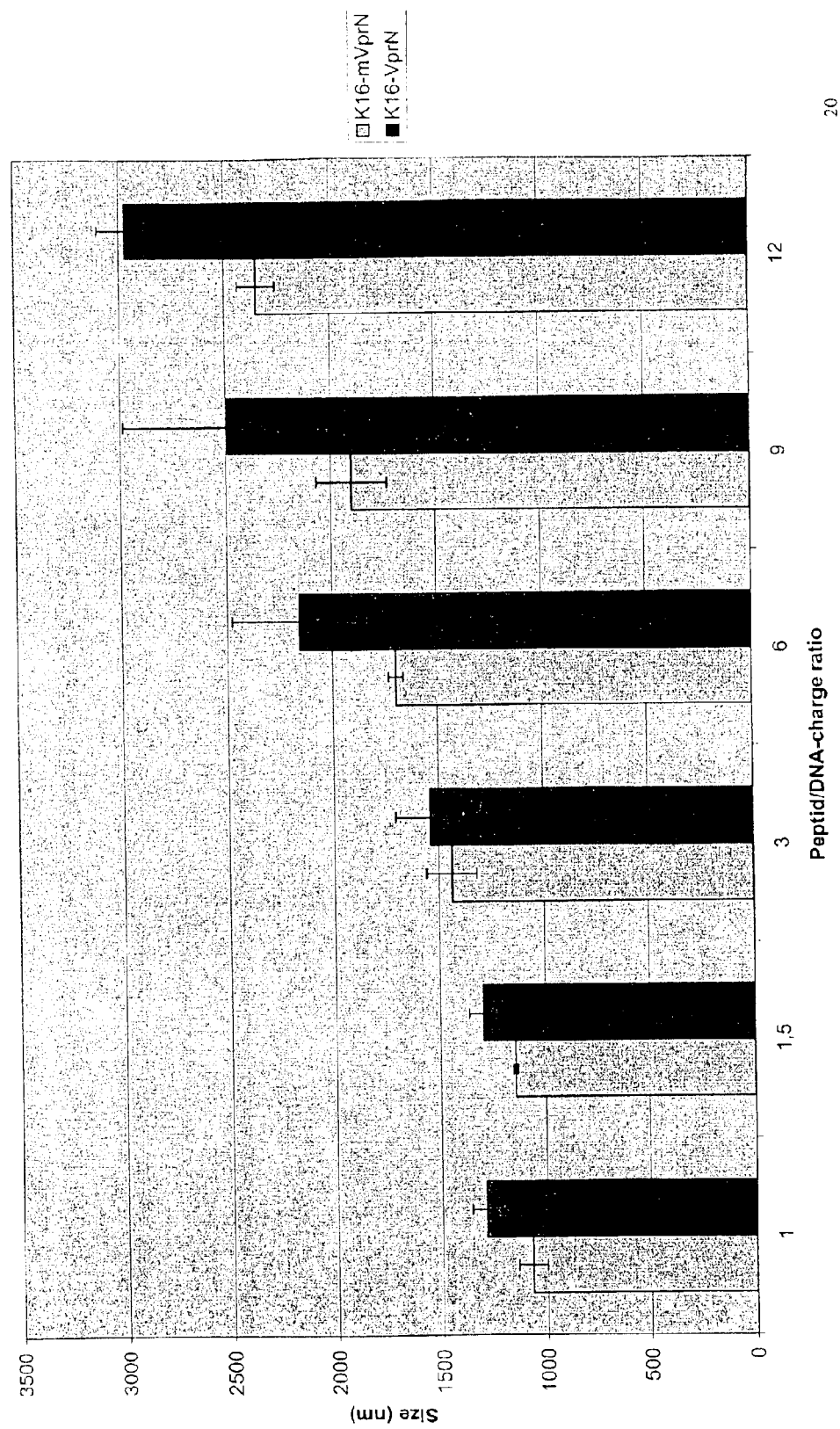
FIG. 11 shows apparent size.
Figure 12:
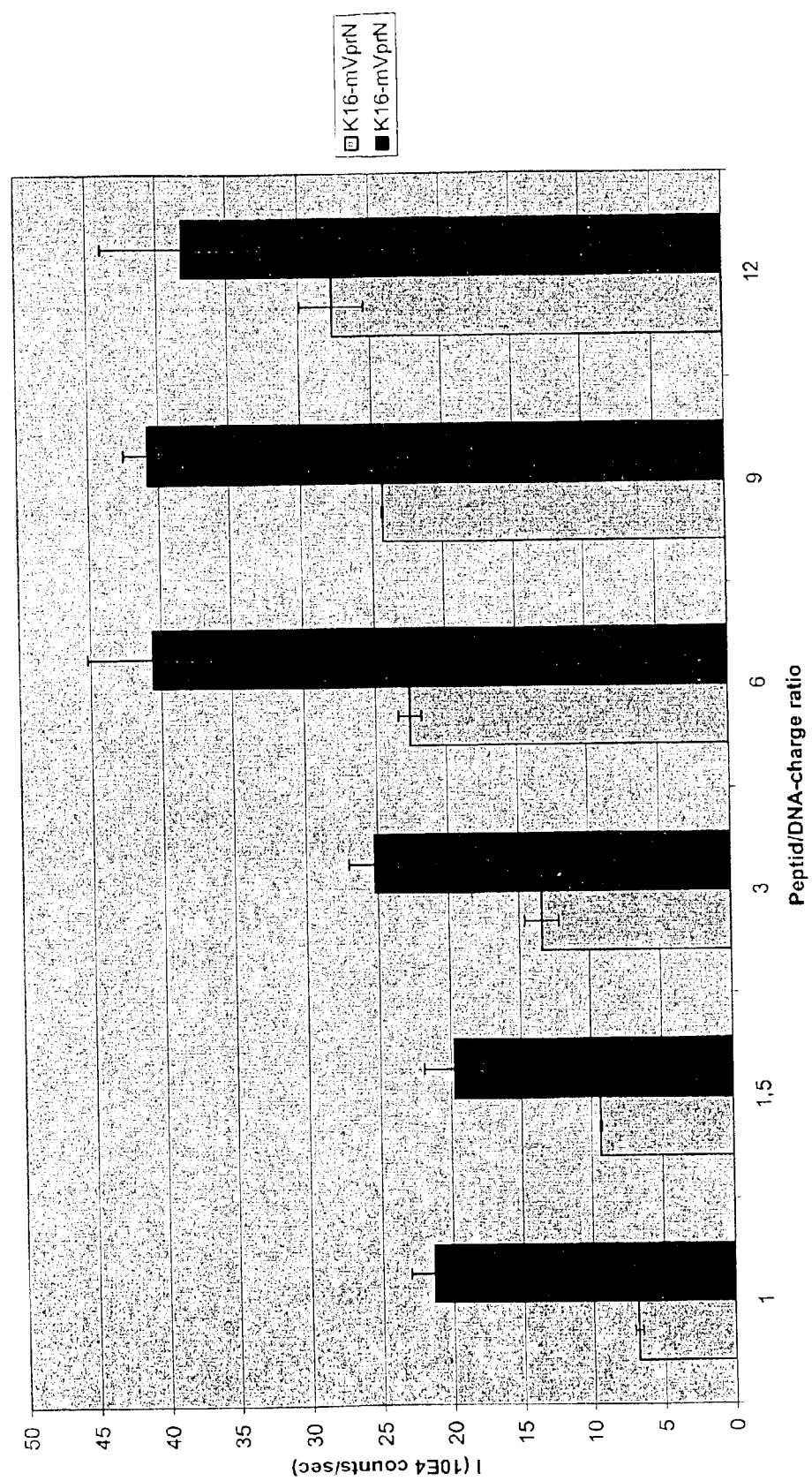
FIG. 12 shows light scattering intensity.

In order to exclude the possibility that the observed enhancement of the transfection efficiency was mainly related to a more favorable complex formation process when using the K16-VprN peptide, size measurements (FIG. 11) and the determination of the relative particle number (FIG. 12) using dynamic light scattering were performed. As shown in FIG. 11, there is no significant difference in the particle size of DNA complexes when K16-VprN was used as compared to K16-mVprN. Moreover, FIG. 12 shows that light scattering intensity increases with higher peptide to DNA ratios. However, the comparison of FIGS. 10 and 12 clearly shows that the measured light scattering intensities do not correlate with the reporter gene expression. Indeed, at a peptide to DNA charge ratio of 3 the K16-VprN peptide generates a three-fold increase of the light scattering intensity and an increase of the reporter gene expression of at least 100-times, as compared to K16-mVprN. At a peptide to DNA charge ratio of 9 the light scattering intensity increases twice as compared to charge ratio 3. However, in these conditions the reporter gene expression only increases 10 fold.

Figure 13:
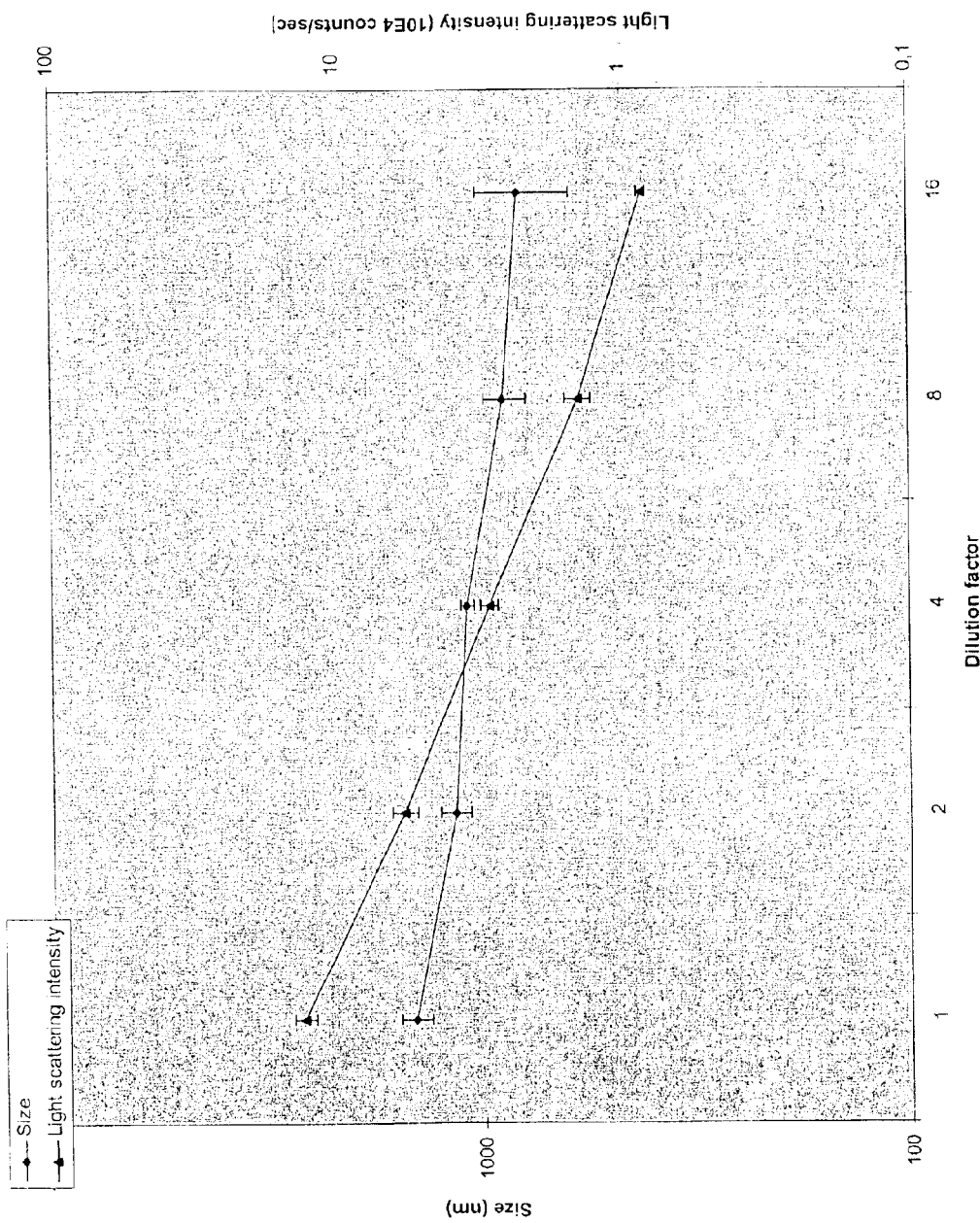
FIG. 13 shows K16-mVprN.
Figure 14:
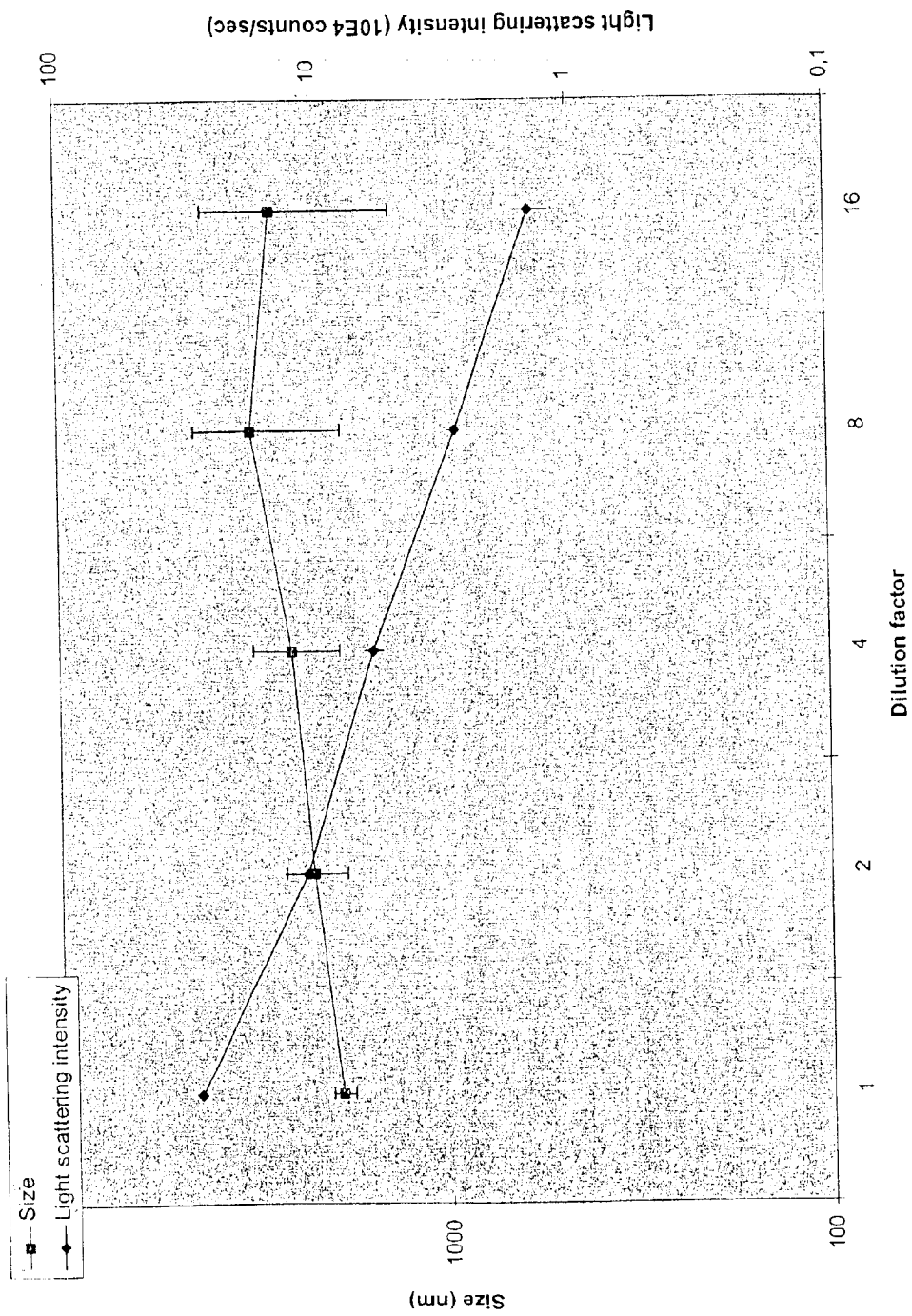
FIG. 14 shows K16-VprN.

In order to demonstrate the correlation between the measured light scattering intensity and the relative amount in DNA-complexes (FIGS. 13 and 14) peptide/DNA-complexes were formed using plasmid DNA together with K16-VprN or K16-mVprN. The complexes were subsequently diluted up to 1:16 and subjected to dynamic light scattering measurements. The result shows that whereas the light scattering intensities decrease with increasing dilutions, the relative size of the complexes remains nearly constant. This observation demonstrates that the light scattering intensity is a measurable indication of the relative amount of DNA complexes.

These results suggest that the observed sequence-specific increase of reporter gene expression generated by the K16-VprN peptide is not due to an increase of the particle size or the particle amount. Consequently, we expect that a cellular mechanism occurs during the transfection process based on the recognition of the VprN-sequence by specific factors. It is likely that the K16-VprN/plasmid DNA-complex is recognized by the nuclear import machinery as an nuclear import substrate. Subsequently, this results in an increased accumulation of the DNA inside the nucleus which finally leads to the observed enhancement of the transfection efficiency.

In terms of novelty, these results show that:
1. a DNA-peptide-lipid complex was formed, the composition of which lead to a sequence specific enhancement of the transfection efficiency which was related to a NLS-sequence.
2. the cyclization of the NLS-sequence further increases the transfection efficiency of the DNA-complex.
3. the utilization of the VprN-sequence increases dramatically the efficiency of the transfection system in a NLS-sequence specific manner.

SEQUENCE LISTING

```
<160> NUMBER OF SEQ ID NOS: 8

<210> SEQ ID NO 1
<211> LENGTH: 28
<212> TYPE: PRT
<213> ORGANISM: Artificial Sequence
<220> FEATURE:
<223> OTHER INFORMATION: Synthetic peptide sequence, K16-NLS, that
      carries 16 lysine residues for the binding of the peptide to the
      plasmid DNA.

<400> SEQUENCE: 1

Cys Lys Lys Lys Lys Lys Lys Lys Lys Lys Lys Lys Lys Lys Lys Lys
1               5                   10                  15

Lys Gly Gly Gly Pro Lys Lys Arg Lys Val Gly
            20                  25

<210> SEQ ID NO 2
<211> LENGTH: 28
<212> TYPE: PRT
<213> ORGANISM: Artificial Sequence
<220> FEATURE:
<223> OTHER INFORMATION: Synthetic peptide sequence, K16-SLN, that
      carries 16 lysine residues for the binding of the peptide to the
      plasmid DNA.

<400> SEQUENCE: 2

Cys Lys Lys Lys Lys Lys Lys Lys Lys Lys Lys Lys Lys Lys Lys Lys
1               5                   10                  15

Lys Gly Gly Gly Gly Val Lys Arg Lys Lys Lys Pro
            20                  25

<210> SEQ ID NO 3
<211> LENGTH: 43
<212> TYPE: PRT
<213> ORGANISM: Artificial Sequence
<220> FEATURE:
<223> OTHER INFORMATION: Synthetic peptide sequence, K16-Vpr, that
      carries 16 lysine residues for the binding of the peptide to the
      plasmid DNA.

<400> SEQUENCE: 3

Lys Lys Lys Lys Lys Lys Lys Lys Lys Lys Lys Lys Lys Lys Lys Lys
1               5                   10                  15

Cys Gly Gly Gly Ile Gly Cys Arg His Ser Arg Ile Gly Val Thr Arg
            20                  25                  30

Gln Arg Arg Ala Arg Asn Gly Ala Ser Arg Ser
        35                  40

<210> SEQ ID NO 4
<211> LENGTH: 39
<212> TYPE: PRT
<213> ORGANISM: Artificial Sequence
<220> FEATURE:
```

```
<223> OTHER INFORMATION: Synthetic peptide sequence, K16-VprN, that
      carries 16 lysine residues for the binding of the peptide to the
      plasmid DNA.

<400> SEQUENCE: 4

Lys Lys Lys Lys Lys Lys Lys Lys Lys Lys Lys Lys Lys Lys Lys Lys
1               5                   10                  15

Gly Gly Gly Cys Asn Glu Trp Thr Leu Glu Leu Leu Glu Glu Leu Lys
            20                  25                  30

Asn Glu Ala Val Arg His Phe
        35

<210> SEQ ID NO 5
<211> LENGTH: 38
<212> TYPE: PRT
<213> ORGANISM: Artificial Sequence
<220> FEATURE:
<223> OTHER INFORMATION: Synthetic peptide sequence, K16-mVprN, that
      carries 16 lysine residues for the binding of the peptide to the
      plasmid DNA.

<400> SEQUENCE: 5

Lys Lys Lys Lys Lys Lys Lys Lys Lys Lys Lys Lys Lys Lys Lys Lys
1               5                   10                  15

Gly Gly Gly Asn Glu Ala Thr Leu Glu Leu Leu Pro Glu Leu Lys Asn
            20                  25                  30

Pro Ala Val Arg His Phe
        35

<210> SEQ ID NO 6
<211> LENGTH: 14
<212> TYPE: PRT
<213> ORGANISM: Artificial Sequence
<220> FEATURE:
<223> OTHER INFORMATION: Cyclic NLS-sequence of the K16-Cyc
      synthetic peptide
<400> SEQUENCE: 6

Val Lys Leu Lys Val Tyr Pro Leu Lys Lys Lys Arg Lys Pro
1               5                   10

<210> SEQ ID NO 7
<211> LENGTH: 17
<212> TYPE: PRT
<213> ORGANISM: Artificial Sequence
<220> FEATURE:
<223> OTHER INFORMATION: Oligo-lysine DNA-binding domain of the K16-Cyc
      synthetic peptide

<400> SEQUENCE: 7

Lys Lys Lys Lys Lys Lys Lys Lys Lys Lys Lys Lys Lys Lys Lys Lys
1               5                   10                  15

Cys

<210> SEQ ID NO 8
<211> LENGTH: 7
<212> TYPE: PRT
<213> ORGANISM: Artificial Sequence
<220> FEATURE:
<223> OTHER INFORMATION: The SV 40-NLS sequence contained in the
      synthetic peptide sequence, K16-NLS

<400> SEQUENCE: 8

Pro Lys Lys Lys Arg Lys Val
1               5
```

What is claimed is:

1. A method for transfection, comprising the step of transfecting a cell with a complex comprising plasmid DNA, a synthetic peptide K16-CYC comprising the following sequence:

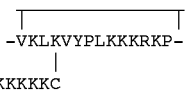

```
-VKLKVYPLKKKRKP-        (SEQ ID NO:6)
 |
KKKKKKKKKKKKKKKC        (SEQ ID NO:7),
``` and a lipid.

2. The method according to claim 1, wherein the lipid is a cationic liposome.

3. The method according to claim 1, wherein the ratio of the peptide to DNA charge is 0.7 to 1.0.

4. The method according to claim 1, wherein the ratio of the plasmid DNA to lipid weight is 2:1 to 1:1.

5. A cyclic peptide K16-CYC.

6. A method for transfection, comprising the step of transfecting a cell with a complex comprising a synthetic peptide K16-CYC comprising the following sequence:

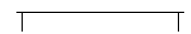

```
-VKLKVYPLKKKRKP-        (SEQ ID NO:6)
 |
KKKKKKKKKKKKKKKC        (SEQ ID NO:7),
``` and a plasmid DNA for transfection.

* * * * *